United States Patent [19]

Baget

[11] 3,961,055

[45] June 1, 1976

[54] HYDROXY AND ETHER CONTAINING PHENOTHIAZINE DERIVATIVES

[75] Inventor: Jean Baget, Sceaux, France

[73] Assignee: Rhone-Poulenc Industries, Paris, France

[22] Filed: Jan. 21, 1975

[21] Appl. No.: 542,799

[30] Foreign Application Priority Data
Jan. 22, 1974 France .............................. 74.02101
Nov. 12, 1974 France .............................. 74.37295

[52] U.S. Cl. .......................... 424/247; 260/243 A
[51] Int. Cl.² ................ A61K 27/00; C07D 279/28
[58] Field of Search .............. 260/243 A; 424/247, 424/10 H

[56] References Cited
UNITED STATES PATENTS

| | | | |
|---|---|---|---|
| 3,150,129 | 9/1964 | Jacob et al. | 260/243 A |
| 3,879,551 | 4/1975 | Blondel et al. | 424/24.D |

FOREIGN PATENTS OR APPLICATIONS

| | | | |
|---|---|---|---|
| 1,558,912 | 1/1969 | France | 260/243 A |

Primary Examiner—Henry R. Jiles
Assistant Examiner—R. W. Ramsuer
Attorney, Agent, or Firm—Stevens, Davis, Miller & Mosher

[57] ABSTRACT

Phenothiazine derivatives of the formula:

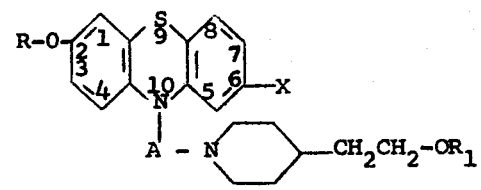

wherein X represents methylthio, methylsulphonyl or dimethylsulphamoyl, R represents hydrogen, alkyl of 1 through 10 carbon atoms, phenylalkyl containing 1 through 4 carbon atoms in the alkyl part, or tetrahydropyranyl, A represents $-(CH_2)_3-$ or $-CH_2-CH(CH_3)-CH_2-$, and $R_1$ represents hydrogen, alkanoyl containing 1 through 16 carbon atoms in the alkyl part or alkenoyl containing 2 through 16 carbon atoms in the alkenyl part, are new compounds possessing pharmacodynamic properties; they are particularly active as anti-emetic agents.

12 Claims, No Drawings

HYDROXY AND ETHER CONTAINING PHENOTHIAZINE DERIVATIVES

This invention relates to new derivatives of phenothiazine.

During the past thirty years considerable research and experimentation have been conducted in the field of N-substituted phenothiazine derivatives and certain of these compounds have been found to possess valuable therapeutic properties. Some are useful primarily on account of outstanding antihistaminic activity, others because of their tranquillising action and of their efficacy as anti-shock agents and yet others are, for example, effective agents for controlling or minimising motion-sickness. It has nevertheless been demonstrated that of the very large number of possible N-substituted phenothiazine compounds that have been proposed or tested by various workers, only comparatively few types have useful application in human or veterinary medicine and that both the nature and the degree of useful effect can radically alter even with apparently small changes in chemical structure.

It is an object of the present invention to provide new phenothiazine derivatives which possess unexpectedly useful pharmacological properties of a nature hereinafter referred to in detail and of a degree of activity that could not have been predicted from knowledge of their chemical structure.

The phenothiazine derivatives of the present invention are those which conform to the general formula:

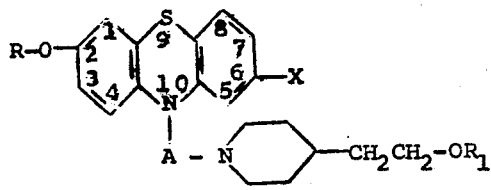

wherein X represents a methylthio, methylsulphonyl or dimethylsulphamoyl radical, R represents a hydrogen atom or an alkyl radical containing 1 to 10 carbon atoms, a phenylalkyl radical containing 1 to 4 carbon atoms in the alkyl part (preferably benzyl), or a tetrahydropyranyl radical, A represents —(CH$_2$)$_3$— or —CH$_2$—CH(CH$_3$)—CH$_2$— (preferably —(CH$_2$)$_3$—), and R$_1$ represents a hydrogen atom or an alkanoyl radical containing 1 to 16 carbon atoms in the alkyl part or an alkenoyl radical containing 2 to 16 carbon atoms in the alkenyl part, and acid addition salts thereof. The numbering of the positions of the phenothiazine ring is in accordance with Beilstein.

According to a feature of the present invention, the phenothiazine derivatives of general formula I, wherein R represents an alkyl radical containing 1 to 10 carbon atoms, a phenylalkyl radical containing 1 to 4 carbon atoms in the alkyl part, or a tetrahydropyranyl radical, R$_1$ represents a hydrogen atom and the symbols X and A are as hereinbefore defined, are prepared by the process which comprises reacting a phenothiazine derivative of the general formula:

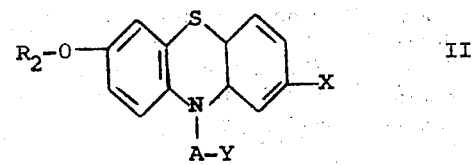

[wherein X and A are as hereinbefore defined, R$_2$ represents an alkyl radical containing 1 to 10 carbon atoms, a phenylalkyl radical containing 1 to 4 carbon atoms in the alkyl part, or a tetrahydropyranyl radical, and Y represents the acid residue of a reactive ester such as a halogen (preferably chlorine) atom or a sulphuric or sulphonic acid ester radical, e.g. the methanesulphonyloxy or toluene-p-sulphonyloxy group] with 4-(2-hydroxyethyl)piperidine. The reaction is generally carried out in an organic solvent, e.g. dimethylformamide, in the presence of an alkaline condensation agent, e.g. sodium bicarbonate, and at a temperature between 50°C. and the boiling point of the reaction mixture.

The phenothiazine derivatives of general formula II can be prepared by the reaction of a compound of the general formula:

(wherein A is as hereinbefore defined, and the symbols Y and Y$_1$, which are preferably different, each represent a halogen atom or a sulphuric or sulphonic acid ester radical) with a compound of the general formula:

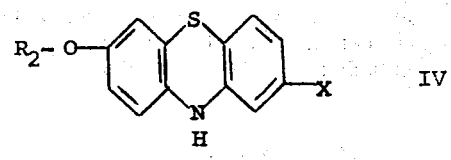

wherein X and R$_2$ are as hereinbefore defined. The reaction is generally carried out in an organic solvent such as a ketone, e.g. methyl ethyl ketone, in the presence of an alkaline condensation agent, e.g. potassium hydroxide.

The compounds of general formula IV wherein X represents a methylthio or dimethylsulphamoyl radical can be prepared by etherification of a phenothiazine of the general formula:

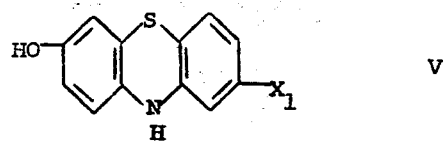

wherein X$_1$ represents a methylthio or dimethylsulphamoyl radical, by means of an alkylating agent such as a dialkyl sulphate or an alkyl or phenylalkyl halide when R$_2$ in formula IV represents an alkyl or phenylalkyl radical or by means of dihydropyran when R$_2$ represents a tetrahydropyranyl radical. Etherification using a dialkyl sulphate or an alkyl or phenylalkyl halide is generally effected in an organic solvent such as a ketone, e.g. methyl ethyl ketone, in the presence of an alkaline condensation agent such as an alkali metal carbonate, e.g. sodium carbonate. Etherification using dihydropyran is generally effected in an anhydrous acid medium, such as a solution of hydrogen chloride in ethanol or in methanol, in the presence of an excess of dihydropyran.

The compounds of general formula V can be prepared by the reduction of a phenothiazinone of the general formula:

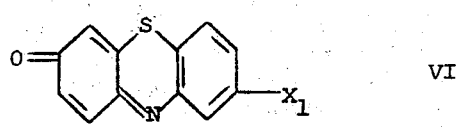

wherein $X_1$ is as hereinbefore defined. The reduction is generally effected by means of sodium hydrosulphite in an organic or aqueous-organic solvent. Alcohols such as ethanol or ketones such as methyl ethyl ketone can be used as organic solvents.

The phenothiazinone of general formula VI wherein $X_1$ represents the dimethylsulphamoyl radical can be prepared by oxidation of 3-dimethylsulphamoylphenothiazine. Ferric chloride in an aqueous medium at a temperature of about 20°C is generally used as the oxidising agent.

The phenothiazinone of the general formula VI wherein X represents the methylthio radical can be prepared by the reaction of the zinc salt of 2-amino-4-methylthio-thiophenol with 2-chlorohydroquinone in the presence of oxygen.

The compounds of general formula IV wherein X represents a methylsulphonyl radical can be prepared from compounds of general formula IV wherein X represents the methylthio radical by carrying out sequentially the following reactions:

According to another feature of the present invention, the phenothiazine derivatives of general formula I wherein $R_1$ represents an alkanoyl radical containing 1 to 16 carbom atoms in the alkyl part or an alkenoyl radical containing 2 to 16 carbon atoms in the alkenyl part and R represents an alkyl radical containing 1 to 10 carbon atoms in the alkyl part, a phenylalkyl radical containing 1 to 4 carbon atoms in the alkyl part or a tetrahydropyranyl radical, the symbols X and A being as hereinbefore defined, are prepared by the process which comprises reacting a corresponding phenothiazine derivative of general formula I, wherein X, A and R are as just stated above and $R_1$ represents a hydrogen atom, with a compound of the general formula:

$$R_3 - CO - Z \qquad XI$$

wherein $R_3$ represents an alkyl radical containing 1 to 16 carbon atoms or an alkenyl radical containing 2 to 16 carbon atoms, and Z represents a reactive radical such as a halogen atom, the hydroxy radical, a lower alkoxy radical containing 1 to 4 carbon atoms, an imidazolyl radical, or an alkanoyloxy or alkenoyloxy radical which can, in particular, be such that the compound $R_3$—CO—Z represents the acid anhydride of the formula $R_3 - CO - O - CO - R_3$.

When the symbol Z represents a halogen atom, and in particular a chlorine atom, it is advantageous to carry out the reaction in an inert organic solvent, for example benzene, toluene or chloroform, at the boiling point of the solvent and in the presence or absence of

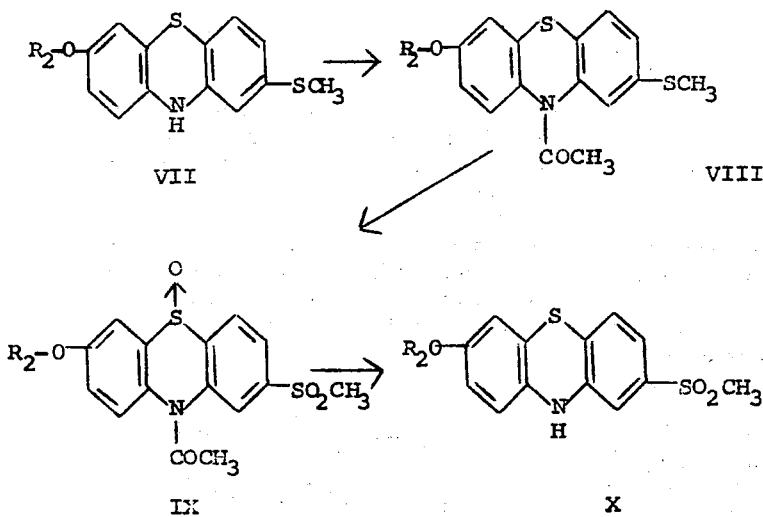

wherein $R_2$ is as hereinbefore defined.

The acetylation of the phenothiazines of formula VII can be effected by means of acetic anhydride.

The oxidation of the phenothiazines of formula VIII to yield phenothiazines of formula IX can be effected in accordance with the usual methods for oxidising a methylthio radical to a methylsulphonyl radical. Hydrogen peroxide in a basic medium is preferably used.

The reduction of the phenothiazines of formula IX to yield the phenothiazines of formula X can be effected in accordance with known methods which make it possible to reduce a sulphoxide and to remove an acetyl radical without affecting the rest of the molecule. Zinc in the presence of acetic acid, optionally in an organic solvent such as dimethylformamide, is preferably used.

an inorganic or organic basic acid-binding agent.

When the symbol Z represents the hydroxy radical, the reaction is generally carried out in an inert organic solvent, for example tetrahydrofuran, benzene, chloroform or dimethylformamide, in the presence either of a strong acid or a Lewis acid, or dicyclohexylcarbodiimide.

When the symbol Z represents a lower alkoxy radical, the reaction is generally carried out in an inert organic solvent, for example toluene, and the alcohol formed is removed by azeotropic distillation.

When the symbol Z represents an imidazolyl radical, the reaction is generally carried out in an inert organic solvent, for example benzene, tetrahydrofuran or chloroform, in the presence of sodium ethoxide at a temperature of about 20°C.

When the symbol Z represents an alkanoyloxy or alkenoyloxy radical, the reaction is carried out in the presence or absence of an inert organic solvent, for example chloroform, at a temperature between 50°C and the boiling point of the reaction mixture.

According to a still further feature of the present invention, the phenothiazine derivatives of general formula I, wherein R represents a hydrogen atom and the symbols X, A and $R_1$ are as hereinbefore defined, are prepared from a corresponding phenothiazine derivative of general formula I, wherein X, A and $R_1$ are as hereinbefore defined and R represents an alkyl radical containing 1 to 10 carbon atoms, a phenylalkyl radical containing 1 to 4 carbon atoms in the alkyl part, or a tetrahydropyranyl radical, in accordance with known methods for the replacement of an alkoxy, phenylalkoxy or tetrahydropyranyloxy radical by a hydroxy radical without affecting the rest of the molecule. By the term "known methods" as used in this specification is meant methods heretofore used or described in the chemical literature.

Generally the reaction is carried out in an acid medium in the presence of an organic solvent. A phenothiazine derivative of general formula I wherein R represents an isopropyl, benzyl or tetrahydropyranyl radical is preferably used, working in an organic solvent, e.g. chloroform, in the presence of sulphuric acid, and at a temperature between −10 and +10°C.

The phenothiazine derivatives of general formula I obtained by the aforementioned processes can optionally be purified by physical methods such as distillation, crystallisation or chromatography, or by chemical methods such as the formation of salts, crystallisation of the salts and decomposition of them in an alkaline medium. In carrying out the said chemical methods the nature of the anion of the salt is immaterial, the only requirement being that the salt must be well-defined and readily crystallisable.

The phenothiazine derivatives of general formula I can be converted by known methods into acid addition salts. The acid addition salts can be obtained by the action of acids on the phenothiazine bases in appropriate solvents. As organic solvents there may be used, for example, alcohols, ethers, ketones or chlorinated hydrocarbons. The salt which is formed is precipitated, if necessary after concentrating its solution, and is isolated by filtration or decantation.

The phenothiazine derivatives of general formula I and their acid addition salts possess useful pharmacodynamic properties: they are particularly active as anti-emetic agents.

The phenothiazine derivatives of general formula I wherein $R_1$ represents a hydrogen atom manifest powerful and specific anti-emetic activity, that is to say they are devoid of secondary central activity. In the dog, they have shown particularly valuable anti-emetic activity when administered orally or subcutaneously at doses of between 0.005 and 0.5 mg/kg. animal body weight.

The phenothiazine derivatives of general formula I wherein $R_1$ represents an alkanoyl or alkenoyl radical have a long-lasting anti-emetic action. They have given good results in physiological experiments on animals when administered subcutaneously or intramuscularly at doses of 0.010 to 2.0 mg/kg animal body weight.

The phenothiazine derivatives of general formula I wherein R represents a hydrogen atom or an alkyl radical containing 1 to 7 carbon atoms, $R_1$ represents a hydrogen atom or an alkanoyl radical containing 1 to 6 carbon atoms in the alkyl part, or an alkenoyl radical containing 2 to 10 carbon atoms in the alkenyl part, X represents the dimethylsulphamoyl radical and A represents $-(CH_2)_3-$, are of particular interest. Examples of such compounds are 2-methoxy-6-dimethylsulphamoyl-10-3-(4-hydroxyethylpiperidino)propyl]-phenothiazine, 2-isopropoxy-6-dimethylsulphamoyl-10-[3-(4-hydroxyethylpiperidino)-propyl]phenothiazine, 2-heptyloxy-6-dimethylsulphamoyl-10-[3-(4-hydroxyethylpiperidino)propyl]phenothiazine, 2-methoxy-6-dimethylsulphamoyl-10-[3-(4-heptanoyloxyethylpiperidino)propyl]phenothiazine, 2-methoxy-6-dimethylsulphamoyl-10- 3-[4-(undec-10-enoyl)oxyethylpiperidino]-propyl phenothiazine, 2-methoxy-6-dimethylsulphamoyl-10-[3-(4-acetoxyethylpiperidino)propyl]phenothiazine and 2-hydroxy-6-dimethylsulphamoyl-10-[3-(4-hydroxyethylpiperidino)propyl]phenothiazine.

For therapeutic purposes, the bases of general formula I are employed as such or in the form of nontoxic acid addition salts, e.g. salts containing anions which are relatively innocuous to the animal organism in therapeutic doses of the salts (such as hydrochlorides and other hydrohalides, phosphates, nitrates, sulphates, acetates, propionates, succinates, benzoates, fumarates, maleates, tartrates, methanesulphonates, ethanedisulphonates, chlorotheophyllinates, theophylline-acetates, salicylates, phenolphthalinates, and methylene-bis-$\beta$-hydroxynaphthoates) so that the beneficial physiological properties inherent in the bases are not vitiated by side-effects ascribable to the anions.

The following non-limitative Examples, and in which the numbering of the positions of the phenothiazine ring is that of Beilstein, illustrate the invention.

EXAMPLE 1

A mixture of 2-methoxy-6-dimethylsulphamoyl-10-(3-chloropropyl)phenothiazine (44.4 g.), 4-hydroxyethylpiperidine (13.7 g.) and sodium bicarbonate (35.8 g.) in dimethylformamide (450 cc) is heated at about 130°C. for 7 hours with stirring. After cooling, the solution is evaporated to dryness under reduced pressure (15 mm.Hg) with heating to 65°C. The crude product is taken up in distilled water (600 cc.) and then extracted with methylene chloride (total 450 cc.). The combined organic extracts are washed with water and then acidified by adding a solution of methanesulphonic acid (115.2 g.) in water (600 cc.). This acid solution is extracted with methylene chloride (total 600 cc.).

The aqueous solution obtained is rendered alkaline by adding a 15% solution of sodium hydroxide (colour change of phenolphthalein) and the base which precipitates is then extracted with methylene chloride (total 500 cc.). The organic extract is washed with distilled water (total 600 cc.) and then dried over anhydrous sodium sulphate. The solvent is evaporated under reduced pressure (15 mm.Hg) at 40°C. Crude 2-methoxy-6-dimethylsulphamoyl-10-[3- (4-hydroxyethylpiperidino)propyl]phenothiazine (39.7 g.), in the form of a yellow amorphous powder is thus obtained.

A solution of the crude base obtained above (39.4 g.) in methylene chloride (300 cc.) is chromatographed on a column containing silica gel (400 g.) (height : 500 mm., diameter : 45 mm.); elution is carried out using the following solvents:

| | |
|---|---|
| methylene chloride | 4 liters |
| ethyl acetate | 2 liters |
| ethyl acetate/acetone (80/20 by volume) | 2 liters |
| ethyl acetate/acetone (50/50 by volume) | 1 liter |
| acetone | 3 liters |

The way in which separation is progressing is followed by thin layer chromatography. The acetone eluate containing the purified base is concentrated to dryness under reduced pressure (15 mm.Hg). The purified base (27.6 g.) is obtained in the form of a viscous oil.

The base thus obtained (14.9 g.) is dissolved in boiling ethanol (50 cc.) and then a boiling solution of oxalic acid (2.6 g.) in ethanol (15 cc.) is added. After cooling and the addition of isopropanol (25 cc.), crystallisation begins. The temperature is kept at about 5°C. for 4 hours and then the crystals obtained are filtered off and washed successively with ethanol cooled to 5°C. (30 cc.) and then with isopropanol cooled to 5°C. (75 cc.). After drying under reduced pressure (0.05 mm.Hg) for 16 hours at 55°C., 2-methoxy-6-dimethylsulphamoyl-10-[3-(4-hydroxyethylpiperidino)propyl]phenothiazine oxalate (15.5 g.), melting at 174°–176°C., is obtained.

2-Methoxy-6-dimethylsulphamoyl-10-(3-chloropropyl)phenothiazine (m.p. 124°–126°C.; 62.6 g.) is prepared by reacting 1-bromo-3-chloropropane (147 g.) with 2-methoxy-6-dimethylsulphamoylphenothiazine (84.4 g.) in the presence of powdered potassium hydroxide (25.8 g.) in methyl ethyl ketone (300 cc.).

2-Methoxy-6-dimethylsulphamoylphenothiazine (m.p. 196°–198°C.; 79.6 g.) is prepared by methylation, using dimethyl sulphate (74.5 g.), of 2-hydroxy-6-dimethylsulphamoylphenothiazine (168 g.) in the presence of powdered sodium hydroxide (30.8 g.) suspended in methyl ethyl ketone (1,820 cc.).

2-Hydroxy-6-dimethylsulphamoylphenothiazine (m.p. 208°–210°C.; 207.6 g.) is prepared by reducing 6-dimethylsulphamoylphenothiazin-2-one (250 g.) by means of sodium hydrosulphite (190 g.) in a mixture of methyl ethyl ketone (1,350 cc.) and distilled water (450 cc.).

6-Dimethylsulphamoylphenothiazine-2-one (m.p. 244°–245°C.; 320 g.) is prepared by oxidising 3-dimethylsulphamoylphenothiazine (570 g.) by means of a solution of ferric chloride (1,382 g.) in distilled water (2,000 cc.).

EXAMPLE 2

A mixture of 2-methoxy-6-methylthio-10-(3-chloropropyl)phenothiazine (9.2 g.), 4-hydroxyethylpiperidine (3.2 g.) and sodium bicarbonate (8.4 g.) in dimethylformamide (90 cc.) is heated at 120°C., with stirring, for 6 hours. The solvent is then evaporated under reduced pressure (0.1 mm.Hg) at 60°C. The residue is taken up in chloroform (80 cc.) and distilled water (80 cc.) and purification of the product is effected by making the medium acidic and then reprecipitating the base by the procedure mentioned in Example 1. 2-Methoxy-6-methylthio-10-[3-(4-hydroxyethylpiperidino)propyl]-phenothiazine (7.9 g.) in the crude state, in the form of an amorphous beige powder, is thus obtained. This powder is taken up in boiling acetonitrile (15 cc.). After cooling of the solution for 7 hours at a temperature of about 20°C., the crystals which have formed are filtered off, washed with acetonitrile (10 cc.) and with diethyl ether (60 cc.) and then dried at 45°C. under reduced pressure (0.05 mm.Hg) for 17 hours. 2-Methoxy-6-methylthio-10-[3-(4-hydroxyethylpiperidino)propyl]-phenothiazine (7.37 g.), melting at 101°–103°C., is obtained.

2-Methoxy-6-methylthio-10-(3-chloropropyl)-phenothiazine (10.1 g.) is prepared by reacting 1-bromo-3-chloropropane (47.5 g.) with 2-methoxy-6-methylthiophenothiazine (22.0 g.).

2-Methoxy-6-methylthiophenothiazine (m.p. 152°–154°C.; 20.1 g.) is prepared by methylation of 2-hydroxy-6-methylthiophenothiazine (37.8 g.) by means of dimethyl sulphate (22.2 g.) in the presence of sodium carbonate (30.1 g.) in acetone.

2-Hydroxy-6-methylthiophenothiazine (m.p. 188°–190°C.; 37.8 g.) is prepared by reacting the zinc salt of 2-amino-4-methylthiothiophenol (45.0 g.) with 2-chlorohydroquinone (m.p. 106°–108°C.; 64.0 g.) in the presence of sodium hydroxide pellets (17.8 g.) under a stream of oxygen. The phenothiazinone obtained is then reduced in situ by means of sodium hydrosulphite (81.0 g.).

2-Amino-4-methylthiothiophenol can be prepared in accordance with the method of Bourquin et al., Helv. Chim. Acta, 42, 2546 (1959).

EXAMPLE 3

A mixture of 2-methoxy-6-methylsulphonyl-10-(3-chloropropyl)phenothiazine (13.7 g.), 4-hydroxyethylpiperidine (4.7 g.) and sodium bicarbonate (12.0 g.) in dimethylformamide (125 cc.) is heated, with stirring, for 7 hours at 125°C. By following the procedure of Example 1 thereafter, a crude base (13.8 g.) is obtained. This base dissolved in methylene chloride (150 cc.) is chromatographed on a column (height : 450 mm., diameter : 27 mm.) containing silica gel (130 g.), eluting with the following solvents:

| | |
|---|---|
| methylene chloride | 300 cc. |
| methylene chloride/ethyl acetate (50/50 by volume) | 300 cc. |
| ethyl acetate | 900 cc. |
| ethyl acetate/acetone (50/50 by volume) | 300 cc. |
| acetone | 900 cc. |

The way in which separation is progressing is followed by thin layer chromatography. The fractions corresponding to elution with pure ethyl acetate and with ethyl acetate/acetone are combined and the solvents are evaporated under reduced pressure (15 mm.Hg). The purified base (9.65 g.), in the form of a yellow-orange oil, is obtained.

This base is dissolved in anhydrous diethyl ether (185 cc.). After 24 hours at a temperature of about 20°C. followed by 7 hours at 5°C., the crystals which have formed are filtered off, washed with diethyl ether (total 200 cc.) and dried at 45°C. under reduced pressure (0.01 mm.Hg) for 18 hours. 2-Methoxy-6-methylsulphonyl-10-[3-(4-hydroxyethylpiperidino)propyl]-phenothiazine (8.0 g.), melting at 117°–118°C., is obtained.

2-Methoxy-6-methylsulphonyl-10-(3-chloropropyl)-phenothiazine (m.p. 122°–124°C.; 15.0 g.) is prepared by reacting 1-bromo-3-chloropropane (30.4 g.) with 2-methoxy-6-methylsulphonylphenothiazine (15.9 g.) in the presence of 85% pure ground potassium hydroxide (5.6 g.) dissolved in methyl ethyl ketone (75 cc.).

2-Methoxy-6-methylsulphonylphenothiazine (m.p. 204°–206°C.; 16.05 g.) is prepared by reduction of 2-methoxy-6-methylsulphonyl-9-oxophenothiazine (47 g.) by means of zinc powder (28 g.) in dimethylformamide (175 cc.), acetic acid (73 cc.) and distilled water (73 cc.).

2-Methoxy-6-methylsulphonyl-9-oxaphenothiazine (m.p. higher than 280°C.; 48 g.) is prepared by oxidation of 2-methoxy-6-methylthio-10-acetylphenothiazine (m.p. 106°–108°C.; 55.0 g.) dissolved in 95% ethanol (95 cc.) by means of 130 volumes hydrogen peroxide (842 cc.). The crude 2-methoxy-6-methylsulphonyl-9-oxo-10-acetylphenothiazine obtained (m.p. about 160°C.) is saponified by means of an alcoholic solution of potassium hydroxide (11.2 g.) in ethanol (200 cc.).

2-Methoxy-6-methylthio-10-acetylphenothiazine (m.p. 106°–108°C.; 29.6 g.) is prepared by acetylation of 2-methoxy-6-methylthiophenothiazine (m.p. 152°–154°C.; 26.2 g.) by means of acetic anhydride.

EXAMPLE 4

A mixture of 2-isopropoxy-6-dimethylsulphamoyl-10-(3-chloropropyl)phenothiazine (27.8 g.), 4-hydroxyethylpiperidine (8.2 g.) and sodium bicarbonate (21.1 g.) in dimethylformamide (265 cc.) is heated at 130°C. for 7 hours. The reaction mixture is then treated under the conditions mentioned in Example 1. The purified base (15 g.) is thus obtained and, on lyophilisation of an aqueous solution of its hydrochloride, yields 2-isopropoxy-6-dimethylsulphamoyl-10-[3-(4-hydroxyethylpiperidino)propyl]phenothiazine hydrochloride (11.6 g.) melting at about 140°C.

Crude 2-isopropoxy-6-dimethylsulphamoyl-10-(3-chloropropyl)phenothiazine (60.8 g.) is prepared by reacting 1-bromo-3-chloropropane (80.8 g.) with 2-isopropoxy-6-dimethylsulphamoylphenothiazine (m.p. 187°–189°C.; 52.0 g.).

2-Isopropoxy-6-dimethylsulphamoylphenothiazine (42.8 g.) is prepared by reacting 2-iodopropane (33.8 g.) with 2-hydroxy-6-dimethylsulphamoylphenothiazine (40.0 g.) prepared as indicated in Example 1.

EXAMPLE 5

A mixture of 2-isopropoxy-6-methylsulphonyl-10-(3-chloropropyl)phenothiazine (20 g.), 4-hydroxyethylpiperidine (6.4 g.) and sodium bicarbonate (16.5 g.) in dimethylformamide (170 cc.) is heated at 150°C. for 7 hours 30 minutes with stirring. The reaction mixture is then treated under the conditions mentioned in Example 1. 2-Isopropoxy-6-methylsulphonyl-10-[3-(4-hydroxyethylpiperidino)propyl]phenothiazine (9.0 g.), melting at about 50°C., is thus obtained.

Crude 2-isopropoxy-6-methylsulphonyl-10-(3-chloropropyl)phenothiazine (128 g.) is prepared by reacting 1-bromo-3-chloropropane (100 g.) with 2-isopropoxy-6-methylsulphonylphenothiazine (m.p. 179°–180°C.; 100 g.).

2-Isopropoxy-6-methylsulphonylphenothiazine (21.7 g.) is prepared by reacting 2-iodopropane (17.0 g.) with 2-hydroxy-6-methylsulphonylphenothiazine (m.p. 218°–219°C.; 19.0 g.).

2-Hydroxy-6-methylsulphonylphenothiazine (126 g.) is prepared by reduction of 6-methylsulphonylphenothiazin-2-one (175 g.) dissolved in methyl ethyl ketone (1,550 cc.) by means of sodium hydrosulphite (152.5 g.) in distilled water (525 cc.).

6-Methylsulphonylphenothiazin-2-one (m.p. 275°–280°C.; 130 g.) is prepared by oxidation of 3-methylsulphonylphenothiazine (500 g.) by means of an aqueous solution of ferric chloride ($d$ = 1.45; 2.25 litres).

EXAMPLE 6

A mixture of 2-heptyloxy-6-dimethylsulphamoyl-10-(3-chloropropyl)phenothiazine (24.3 g.), 4-hydroxyethylpiperidine (7.1 g.) and sodium bicarbonate (16.1 g.) in dimethylformamide (180 cc.) is heated at about 130°C. for 8 hours with stirring. After cooling, the reaction mixture is evaporated to dryness under reduced pressure (15 mm.Hg) with heating to 65°C. The residue is taken up in distilled water (300 cc.) and then extracted with methylene chloride (total 560 cc.). The combined organic extracts are acidified by addition of a solution of methanesulphonic acid (57.6 cc.) in water (250 cc.). The organic phase is washed with an 8% aqueous solution of sodium hydroxide (total 300 cc.) and then with distilled water (total 1 litre), and is finally dried over sodium sulphate. On evaporation of the solvent under reduced pressure (15 mm. Hg) at 40°C., crude 2-heptyloxy-6-dimethylsulphamoyl-10-[3-(4-hydroxyethylpiperidino)propyl]-phenothiazine (21.1 g.), in the form of a brown viscous oil, is obtained.

A solution of this base (21 g.) in benzene (300 cc.) is chromatographed on a column (height : 450 mm., diameter : 30 mm.) of silica gel (150 g.). Elution is effected using the following solvents:

| | |
|---|---|
| benzene | 1.6 liters |
| benzene/chloroform (50/50 by volume) | 1 liter |
| chloroform | 3 liters |
| chloroform/ethyl acetate (50/50 by volume) | 2 liters |
| chloroform/ethyl acetate (33/66 by volume) | 1 liter |
| ethyl acetate | 3 liters |
| acetone | 1 liter |
| ethanol | 3 liters |

The way in which separation is progressing is followed by thin layer chromatography. The eluates corresponding to elution by pure ethyl acetate and acetone are combined and concentrated under reduced pressure (15 mm. Hg), and then the residue obtained is dried under reduced pressure (0.1 mm. Hg) at 20°C. for 16 hours. The purified base (9.6 g.) is thus obtained. The base obtained (9.2 g.) is dissolved in 0.1N hydrochloric acid (150 cc.) at 30°C., and the resulting solution lyophilised under reduced pressure (0.01 mm. Hg), the operation being completed by drying for 18 hours at 50°C. under reduced pressure (0.05 mm. Hg.) 2Heptyloxy-6-dimethylsulphamoyl-10-[3-(4-hydroxyethylpiperidino)propyl]phenothiazine hydrochloride (8.2 g.), melting at about 80°C., is obtained.

2-Heptyloxy-6-dimethylsulphamoyl-10-(3-chloropropyl)phenothiazine (24.4 g.), in the form of a viscous oil, is prepared by reacting 1-bromo-3-chloropropane (31.3 g.) with 2-heptyloxy-6-dimethylsulphamoylphenothiazine (23.3 g.) in the presence of powdered potassium hydroxide (5.6 g.) in methyl ethyl ketone (700 cc.).

2-Heptyloxy-6-dimethylsulphamoylphenothiazine (m.p. 160°–162°C.; 23.4 g.) is prepared by reacting 1-iodoheptane (8.4 g.) with 2-hydroxy-6-dimethylsulphamoylphenothiazine (76.8 g.) in the presence of powdered potassium hydroxide (41.4 g.) in methyl ethyl ketone (600 cc.).

EXAMPLE 7

A mixture of 2-benzyloxy-6-dimethylsulphamoyl-10-(3-chloropropyl)phenothiazine (48.9 g.), 4-hydroxyethylpiperidine (12.9g.) and sodium bicarbonate (33.6 g.) in dimethylformamide (400 cc.) is heated at 130°C. for 8 hours with stirring. After cooling, the solution is evaporated to dryness under reduced pressure (15 mm. Hg), with heating to 65°C. The crude product is taken up in distilled water (150 cc.) and then extracted with methylene chloride (total 200 cc.). The combined organic extracts are washed with water (total 400 cc.).

The organic extract is dried over anhydrous sodium sulphate. The solvent is evaporated under reduced pressure (15 mm. Hg) at 40°C. Crude 2-benzyloxy-6-dimethylsulphamoyl-10-[3-(4-hydroxyethylpiperidino)-propyl]phenothiazine (58.3 g.) is thus obtained.

This crude product is chromatographed on a column (height : 620 mm., diameter : 27 mm.) containing silica gel (200 g.), eluting with the following solvents:

| | |
|---|---|
| benzene | 600 cc. |
| benzene/methylene chloride (50/50 by volume) | 700 cc. |
| methylene chloride | 200 cc. |
| ethyl acetate | 600 cc. |
| ethyl acetate/acetone (50/50 by volume) | 500 cc. |
| acetone | 1,200 cc. |

The way in which separation is progressing is followed by thin layer chromatography. The eluates corresponding to the last three elution solvents are combined, dried and concentrated under reduced pressure (0.1 mm. Hg) at 20°C. The residue obtained is kept under that pressure and temperature for 20 hours. The amorphous purified base (28.4 g.) is thus obtained.

This base (12.0 g.) is dissolved in anhydrous chloroform (30 cc.) and a 3.5N solution of hydrogen chloride in diethyl ether (5.7 cc.) is then added. The solvents are evaporated under reduced pressure (15 mm. Hg) and the operation is completed by drying under reduced pressure (0.01 mm. Hg) at 20°C. for 18 hours. The amorphous hydrochloride obtained is taken up in distilled water (350 cc.), the solution is decolourized by adding decolourizing charcoal (3 g.) and filtered. The filtrate is lyophilised, the operation being completed by drying under reduced pressure (0.05 l mm. Hg) at 45°C. for 18 hours. 2-Benzyloxy-6-dimethylsulphamoyl-10-[3-(4-hydroxyethylpiperidino)propyl]phenothiazine hydrochloride (10.5 g.), melting at about 140°C., is thus obtained.

2-Benzyloxy-6-dimethylsulphamoyl-10-(3-chloropropyl)phenothiazine (m.p. 124°–126°C.; 89.0 g.) is prepared by reacting 1-bromo-3-chloropropane (92 g.) with 2-benzyloxy-6-dimethylsulphamoylphenothiazine (69.0 g.) in the presence of powdered potassium hydroxide (16.4 g.) in methyl ethyl ketone (230 cc.).

2-Benzyloxy-6-dimethylsulphamoylphenothiazine (m.p. 192°–194°C.; 69.0 g.) is prepared by reacting benzyl chloride (106.0 g.) with 2-hydroxy-6-dimethylsulphamoylphenothiazine (200 g.).

EXAMPLE 8

A mixture of 2-tetrahydropyranyloxy-6-dimethylsulphamoyl-10-(3-chloropropyl)phenothiazine (16.0 g.), 4-hydroxyethylpiperidine (4.3 g.), sodium bicarbonate (11.0 g.) and dimethylformamide (135 cc.) is heated at about 130°C. for 8 hours with stirring. The reaction mixture is evaporated to dryness under reduced pressure (15 mm. Hg) with heating to 65°C., and the residue obtained is taken up in distilled water (150 cc.) and chloroform (150 cc.). The organic phase is decanted, washed with water (200 cc.), dried and then chromatographed on a column (height : 560 mm., diameter : 27 mm.) containing silica gel (220 g.). Elution is effected using the following solvents:

| | |
|---|---|
| chloroform | 3 liters |
| ethyl acetate | 2 liters |
| acetone | 2 liters |
| methanol | 2 liters |

The way in which purification is progressing being followed by thin layer chromatography. The eluates corresponding to elution with ethyl acetate and methanol are combined and concentrated under reduced pressure. After drying under reduced pressure (0.01 mm. Hg) at 35°C., the amorphous purified base (9.6 g.) is obtained.

This base (9.5 g.) is dissolved in boiling acetonitrile (25 cc.). After cooling for 4 hours at +2°C., the crystals which have formed are filtered off and washed with acetonitrile (10 cc.) at 5°C. and then with diisopropyl ether (total 50 cc.). After drying under reduced pressure (0.05 mm. Hg) for 18 hours at 50°C., 2-tetrahydropyranyloxy-6-dimethylsulphamoyl-10-[3-(4-hydroxyethylpiperidino)propyl]phenothiazine (7.0 g.), melting at 129°–131°C., is obtained.

2-Tetrahydropyranyloxy-6-dimethylsulphamoyl-10-(3-chloropropyl)phenothiazine m.p. 150°–152°C.; 15.7 g.) is prepared by reacting dihydropyran (102 g.) with 2-hydroxy-6-dimethylsulphamoyl-10-(3-chloropropyl)-phenothiazine (17.2 g.) in the presence of an 8N solution of hydrogen chloride in ethanol (0.1 cc.).

EXAMPLE 9

Working in the absence of moisture, a mixture of 2-methoxy-6-dimethylsulphamoyl-10-[3-(4-hydroxyethylpiperidino)propyl]phenothiazine (11.4 g.) and heptanoyl chloride (3.8 g.) in toluene (150 cc.) is heated under reflux, with stirring, for 6 hours. After cooling, ethyl acetate (75 cc.) is added and the mixture is then rendered alkaline, without exceeding a temperature of 5°C., by adding a solution of anhydrous sodium carbonate (2.3 g.) in distilled water (75 cc.). After decanting, the aqueous layer is extracted with ethyl acetate (100 cc.). The organic extracts are combined and then washed three times with distilled water (total 240 cc.). The organic extract is dried over sodium sulphate and the solvent evaporated. 2-Methoxy-6-dimethylsulphamoyl-10-[3-(4-heptanoyloxyethylpiperidino)propyl]phenothiazine (14.4 g.), in the crude state, is thus obtained.

A hot solution of oxalic acid (2.0 g.) in ethanol (15 cc.) is added to a boiling solution of the crude base obtained as described above (14.2 g.) in ethanol (25 cc.). The mixture is stirred and then isopropanol (20 cc.) is added. Crystallisation begins and the mixture is cooled for 4 hours at 5°C.; the crystals which have formed are filtered off, washed with ethanol (total 20 cc.) and then with isopropanol (80 cc.), and dried at 55°C. under reduced pressure (0.05 mm. Hg) for 18 hours. 2-Methoxy-6-dimethylsulphamoyl-10-[3-(4-heptanoyloxyethylpiperidino)propyl]phenothiazine oxalate (9.85 g.), melting at 138°–140°C., is thus obtained.

EXAMPLE 10

Following the procedure of Example 9 but starting with 2-methoxy-6-dimethylsulphamoyl-10-[3-(4-hydroxyethylpiperidino)propyl]phenothiazine (13.6 g.), undec-10-enoic acid chloride (6.1 g.) and toluene (175 cc.), 2-methoxy-6-dimethylsulphamoyl-10- 3-[4-(undec-10-enoyl)oxyethylpiperidino]propyl phenothiazine (17.1 g.), in the crude state, is obtained.

The base (17.0 g.) is dissolved in boiling ethyl acetate (25 cc.), and then oxalic acid (2.3 g.) dissolved in boiling ethyl acetate (30 cc.) is added. After cooling, the crystals which have formed are filtered off, washed with ethyl acetate (10 cc.) and dried at 45°C. under reduced pressure (0.05 mm. Hg) for 18 hours. 2-Methoxy-6-dimethylsulphamoyl-10- 3-[4-(undec-10-enoyl)oxyethylpiperidino]propyl phenothiazine oxalate (11.45 g.), melting at 122°–124°C., is obtained.

EXAMPLE 11

Following the procedure of Example 9, but starting with 2-methoxy-6methylthio-10-[3-(4-hydroxyethylpiperidino)propyl]phenothiazine (10.0 g.) and heptanoyl chloride (3.8 g.) in toluene (150 cc.), 2-methoxy-6-methylthio-10-[3-(4-heptanoyloxyethylpiperidino)-propyl]phenothiazine oxalate (11.3 g.), melting at 122°–124°C., is obtained.

EXAMPLE 12

Following the procedure of Example 9 but starting with 2-methoxy-6-methylsulphonyl-10-[3-(4-hydroxyethylpiperidino)propyl] phenothiazine (10.7 g.) and heptanoyl chloride(3.8 g.) in toluene (150 cc.), 2-methoxy-6-methylsulphonyl-10-[3-(4-heptanoyloxyethylpiperidino)propyl]phenothiazine oxalate (11.6 g.), melting at 130°–132°C., is obtained.

EXAMPLE 13

A mixture of 2-benzyloxy-6-dimethylsulphamoyl-10-[3-(4-hydroxyethylpiperidino)propyl]phenothiazine (11.5 g.), acetic anhydride (22.6 g.) and anhydrous pyridine (56.5 g.) is heated at 80°–85°C. for 30 minutes with stirring. The resulting solution is cooled and poured into distilled water (350 cc.) and crushed ice (100 g.), and then extraction is effected using chloroform (total 400 cc.). The combined organic extracts are washed with N hydrochloric acid (total 400 cc.) at 4°C. and then, still at this temperature, successively with distilled water (400 cc.), a 10% aqueous solution of sodium bicarbonate (310 cc.) and finally with distilled water (total 600 cc.). The organic solution is dried over dry sodium sulphate, the solvent evaporated under reduced pressure (15 mm. Hg) without exceeding 45°C., and the product obtained dried for 18 hours at 20°C. under reduced pressure (0.01 mm. Hg). The resulting crude base (10.0 g.) is taken up in chloroform (100 cc.) and then chromatographed on a column (height : 500 mm., diameter : 27 mm.) containing silica gel (140 g.). Elution is carried out using the following solvents:

| | |
|---|---|
| chloroform | 600 cc. |
| ethyl acetate | 900 cc. |
| acetone | 300 cc. |
| methanol | 300 cc. | the way in which separation is progressing being followed by thin layer chromatography. The eluate corresponding to elution with ethyl acetate is evaporated under reduced pressure (15 mm. Hg) at 20°C. An amorphous product (8.2 g.) is obtained, to which di-isopropyl ether (80 cc.) is added. Crystallisation begins on stirring. After decanting, the crystals are taken up in di-isopropyl ether (80 cc.). After 3 hours at a temperature of 2°C., the crystals are filtered off, washed with di-isopropyl ether (total 150 cc.) and dried at 45°C. for 8 hours under reduced pressure (0.05 mm. Hg). 2-Benzyloxy-6-dimethylsulphamoyl-10-[3-(4-acetoxyethylpiperidino)propyl]phenothiazine (5.9 g.), melting at 94°–96°C., is obtained.

EXAMPLE 14

A mixture of 2-methoxy-6-dimethylsulphamoyl-10-[3-(4-hydroxyethylpiperidino)propyl]phenothiazine (17.35 g.), acetic anhydride (32.3 g.) and anhydrous pyridine (80 cc.) is heated at 80°C. for 1 hour with stirring. After cooling, the reaction mixture is poured into distilled water (150 cc.) and the solution evaporated under reduced pressure (0.5 mm. Hg). The dry extract obtained is washed with di-isopropyl ether (total 400 cc.) and then dried under reduced pressure (0.01 mm. Hg) at 50°C. for 18 hours. A viscous oil (21.2 g.) is obtained and is taken up in distilled water (200 cc.) and chloroform (150 cc.); the mixture is stirred at 5°C. with a saturated solution of sodium bicarbonate (120 cc.). The chloroform layer is decanted and washed with distilled water (total 120 cc.). The dried chloroform solution is chromatographed on a column (height : 580 mm., diameter : 28 mm.) containing silica gel (160 g.) eluting with the following solvents:

| | |
|---|---|
| chloroform | 3 liters |
| ethyl acetate | 3 liters |

The eluate corresponding to ethyl acetate is evaporated under reduced pressure (15 mm. Hg) at 45°C. and the product obtained is dried under reduced pressure (0.01 mm. Hg) at 20°C. for 18 hours. An orange oily base (16.3 g.) is obtained.

This base (16 g.) is dissolved in ethanol (50 cc.) and a solution of anhydrous oxalic acid (2.7 g.) in ethanol (15 cc.) is added. After cooling to approximately 2°C. for 6 hours, the crystals which have formed are filtered off, washed with ethanol (total 80 cc.) and then dried under reduced pressure (0.01 mm. Hg) at 50°C. for 18 hours. 2-Methoxy-6-dimethylsulphamoyl-10-[3-(4-acetoxyethylpiperidino)propyl]phenothiazine oxalate (15.6 g.), melting at 148°–150°C., is obtained.

EXAMPLE 15

Concentrated sulphuric acid (109 g.) cooled to 5°C. is added over the course of 30 seconds to a solution, kept at 5°C, of 2-isopropoxy-6-dimethylsulphamoyl-10-[3-(4-hydroxyethylpiperidino)propyl]-phenothiazine (10.9 g.) in anhydrous chloroform (150 cc.). After stirring for 30 seconds at 5°C., the reaction mixture is poured onto crushed ice (150 g.). The pH of the solution is brought to 7.5 by addition of sodium hydroxide solution ($d = 1.33$), whilst cooling, and extraction is effected using chloroform (total 350 cc.). The chloroform solution is dried over anhydrous sodium sulphate (5 g.), the solvent evaporated under reduced pressure and the product obtained dried under reduced pressure (0.05 mm. Hg) at 20°C. The resulting amorphous product (5.1 g.) is dissolved in boiling acetonitrile (35 cc.). After cooling, the crystals which have formed are filtered off, washed with acetonitrile (5 cc.) and dried at 50°C. under reduced pressure (0.05 mm. Hg) for 20 hours. 2-Hydroxy-6-dimethylsulphamoyl-10-[3-(4-hydroxyethylpiperidino)propyl]phenothiazine (3.9 g.), melting at 163°–165°C., is obtained.

The present invention includes within its scope pharmaceutical compositions comprising, as active ingredient, at least one phenothiazine derivative of general formula I, or a non-toxic acid addition salt thereof, in association with a pharmaceutical carrier or coating. The invention includes especially such preparations made up for oral, rectal, parenteral, subcutaneous or intramuscular administration. Compositions containing as the active ingredient a derivative of general formula I wherein $R_1$ represents hydrogen may by administered orally, rectally or parenterally, Compositions containing as active ingredient a derivative of general formula I wherein $R_1$ represents an alkanoyl or alkenoyl radical may be administered subcutaneously or intramuscularly.

Solid compositions for oral administration include tablets, pills, powders and granules. In such solid compositions the active compound is admixed with at least one inert diluent such as sucrose, lactose or starch. The compositions may also comprise, as is normal practice, additional substances other than inert diluents, e.g. lubricating agents, such as magnesium stearate. Liquid compositions for oral administration include pharmaceutically-acceptable emulsions, solutions, suspensions, syrups and elixirs containing inert diluents commonly used in the art, such as water and liquid paraffin. Besides inert diluents such compositions may also comprise adjuvants such as wetting, emulsifying and suspending agents, and sweetening, flavouring and aromatizing agents.

Compositions for rectal administration are suppositories which contain, in addition to the active substance, excipients such as cacao butter or a suitable wax base.

Preparations according to the invention for parenteral administration of the derivatives of general formula I wherein $R_1$ represents a hydrogen atom include sterile aqueous or non-aqueous solutions, suspensions or emulsions. Examples of non-aqueous solvents or vehicles are propylene glycol, polyethylene glycol, vegetable oils such as olive oil, and injectable organic esters such as ethyl oleate. These compositions may also contain adjuvants such as preserving, wetting, emulsifying and dispersing agents. They may be sterilised by, for example, filtration through a bacteria-retaining filter, by incorporation in the compositions of sterilising agents, by irradiation, or by heating. They may also be manufactured in the form of sterile solid compositions, which can be dissolved in sterile water or some other sterile injectable medium immediately before use.

Preparations according to the invention for subcutaneous or intramuscular administration of one or more of the derivatives of general formula I wherein $R_1$ represents an alkanoyl or alkenoyl radical contain the active compound or compounds in the form of bases in an injectable solution which allows a long-lasting effect to be obtained. Examples of suitable solvents are injectable vegetable oils such as sesame oil or olive oil, and injectable organic esters such as ethyl oleate. The solutions may be sterilised by, for example, filtration through a bacteria-retaining filter, by incorporation in the compositions of sterilising agents, by irradiation or by heating.

The phenothiazine derivatives according to the present invention are particularly useful in the treatment of nausea and vomiting of various origins.

The percentage of active ingredient in the compositions of the invention may be varied, it being necessary that it should constitute a proportion such that a suitable dosage shall be obtained. The dosage depends on the desired therapeutic effect, on the route of administration and on the duration of the treatment. In human therapy the compositions when administered orally or rectally to an adult should generally give doses between 0.5 and 50 mg. of active substance per day. Compositions containing derivatives of general formula I wherein $R_1$ represents hydrogen, when administered by injection should give doses between 0.25 and 25 mg. of active substance per day. The doses of derivatives of general formula I wherein $R_1$ represents an alkanoyl or alkenoyl radical are generally between 50 and 500 mg. administered by one intramuscular injection every 8 to 15 days. In general the physician will decide the posology considered appropriate, taking into account the age and weight and other factors intrinsic to the patient being treated.

The following Examples illustrate pharmaceutical compositions according to the invention.

EXAMPLE 16

Tablets containing 10 mg. of active product and having the following composition are prepared in accordance with the usual technique:

| | |
|---|---|
| 2-methoxy-6-dimethylsulphamoyl-10-[3-(4-hydroxyethyl-piperidino)propyl]phenothiazine oxalate | 0.012 g. |
| starch | 0.100 g. |
| precipitated silica | 0.043 g. |
| magnesium stearate | 0.005 g. |

EXAMPLE 17

2-Methoxy-6-dimethylsulphamoyl-10- 3-[4-(undec-10-enoyl)oxyethylpiperidino]propyl phenothiazine (1.25 g.) is dissolved at 40°C. in neutralised sesame oil (100 cc.) with stirring. After cooling, the yellow solution obtained is filtered through a bacteria-retaining filter under a nitrogen pressure of 2 kg./cm². The filtered solution is then dispensed aseptically into 5 cc. ampoules at the rate of 4.1 cc. of solution per ampoule. The ampoules are sealed under nitrogen. Ampoules, each containing the active product (50 mg.), ready for intramuscular administration, are thus obtained.

I claim:
1. A phenothiazine derivative of the formula:

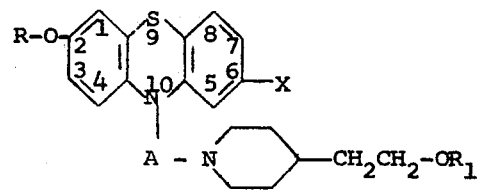

wherein X represents methylthio, methylsulphonyl or dimethylsulphamoyl, R represents hydrogen, alkyl of 1 through 10 carbon atoms, phenylalkyl containing 1 through 4 carbon atoms in the alkyl part, or tetrahydropyranyl, A represents $-(CH_2)_3-$ or $-CH_2-CH(CH_3)-CH_2-$, and $R_1$ represents hydrogen, alkanoyl containing 1 through 16 carbon atoms in the alkyl part, or alkenoyl containing 2 to 16 carbon atoms in the alkenyl part, and non-toxic pharmaceutically acceptable acid addition salts thereof.

2. A phenothiazine compound according to claim 1 wherein R represents alkyl of 1 through 10 carbon atoms, and $R_1$ represents hydrogen, alkanoyl containing 4 through 16 carbon atoms in the alkyl part, or alkenoyl containing 4 through 16 carbon atoms in the alkenyl part.

3. A phenothiazine compound according to claim 1 wherein A represents $-(CH_2)_3-$.

4. A phenothiazine compound according to claim 1 wherein R represents hydrogen or alkyl of 1 through 7 carbon atoms, $R_1$ represents hydrogen or alkanoyl containing 1 through 6 carbon atoms in the alkyl part, or alkenoyl containing 2 through 10 carbon atoms in the alkenyl part, X represents dimethylsulphamoyl, and A represents $-(CH_2)_3-$.

5. The phenothiazine derivative according to claim 1 which is 2-methoxy-6-dimethylsulphamoyl-10-[-3(4-hydroxyethylpiperidino)propyl]phenothiazine and non-toxic pharmaceutically acceptable acid addition salts thereof.

6. The phenothiazine derivative according to claim 1 which is 2-isopropoxy-6-dimethylsulphamoyl-10-[3-(4-hydroxyethylpiperidino)propyl]phenothiazine and non-toxic pharmaceutically acceptable addition salts thereof.

7. The phenothiazine derivative according to claim 1 which is 2-heptyloxy-6-dimethylsulphamoyl-10-[3-(4-hydroxyethylpiperidino)propyl]phenothiazine and non-toxic pharmaceutically-acceptable acid addition salts thereof.

8. The phenothiazine derivative according to claim 1 which is 2-methoxy-6-dimethylsulphamoyl-10-[3-(4-heptanoyloxyethylpiperidino)propyl] phenothiazine and non-toxic pharmaceutically acid addition salts thereof.

9. The phenothiazine derivative according to claim 1 which is 2-methoxy-6-dimethylsulphamoyl-10- 3-[4-(undec-10-enoyl)oxyethylpiperidino]propyl phenothiazine and non-toxic pharmaceutically acceptable acid addition salts thereof.

10. The phenothiazine derivative according to claim 1 which is 2-methoxy-6-dimethylsulphamoyl-10-[3-(4-acetoxyethylpiperidino)propyl]phenothiazine and non-toxic pharmaceutically acceptable acid addition salts thereof.

11. The phenothiazine derivative according to claim 1 which is 2-hydroxy-6-dimethylsulphamoyl-10-[3-(4-hydroxyethylpiperidino)propyl]phenothiazine and non-toxic pharmaceutically acceptable acid addition salts thereof.

12. A pharmaceutical composition having antiemetic activity which comprises as active ingredient, an effective amount of a phenothiazine derivative as claimed in claim 1, or a non-toxic pharmaceutically acceptable acid addition salt thereof, in association with a significant amount of a pharmaceutical carrier.

* * * * *